(12) United States Patent
Yao et al.

(10) Patent No.: US 9,278,164 B2
(45) Date of Patent: Mar. 8, 2016

(54) NEGATIVE PRESSURE WOUND THERAPY SYSTEM

(71) Applicant: APEX MEDICAL CORP., New Taipei (TW)

(72) Inventors: Nan-Kuang Yao, New Taipei (TW); Jhy-Wen Wu, New Taipei (TW); Luo-Hwa Miau, New Taipei (TW); Jen-Chien Chien, New Taipei (TW); Li-Ling Li, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 287 days.

(21) Appl. No.: 13/930,193

(22) Filed: Jun. 28, 2013

(65) Prior Publication Data

US 2013/0289505 A1  Oct. 31, 2013

Related U.S. Application Data

(62) Division of application No. 12/872,973, filed on Aug. 31, 2010, now abandoned.

(51) Int. Cl.
*A61M 1/00* (2006.01)

(52) U.S. Cl.
CPC ............. *A61M 1/0031* (2013.01); *A61M 1/009* (2013.01); *A61M 1/0088* (2013.01); *A61M 1/0066* (2013.01); *A61M 2205/3344* (2013.01); *A61M 2205/3351* (2013.01); *A61M 2205/3355* (2013.01)

(58) Field of Classification Search
CPC ............ A61M 1/0031; A61M 1/0066; A61M 1/0088; A61M 1/009; A61M 2205/3344; A61M 2205/3351; A61M 2205/3355; A61F 13/00068
See application file for complete search history.

(56) References Cited

U.S. PATENT DOCUMENTS

| | | | | |
|---|---|---|---|---|
| 4,798,583 A | * | 1/1989 | Beck et al. | 604/48 |
| 5,407,425 A | * | 4/1995 | Werner et al. | 604/6.07 |
| 2007/0055209 A1 | * | 3/2007 | Patel et al. | 604/315 |
| 2007/0118096 A1 | * | 5/2007 | Smith et al. | 604/541 |
| 2008/0041401 A1 | * | 2/2008 | Casola et al. | 128/897 |
| 2009/0281526 A1 | * | 11/2009 | Kenny et al. | 604/543 |

* cited by examiner

*Primary Examiner* — Philip R Wiest
*Assistant Examiner* — Benjamin Klein
(74) *Attorney, Agent, or Firm* — patenttm.us

(57) ABSTRACT

A negative pressure wound therapy system creates a negative pressure environment in the opening of a wound-dressing unit and a positive pressure environment in the collecting bag. Then a positive pressure detecting procedure is proceeded in the positive pressure environment and a negative pressure detecting procedure is proceeded in the negative pressure environment. The detecting results are sent to determine whether a micro pump is stopped.

9 Claims, 8 Drawing Sheets

NEGATIVE PRESSURE WOUND THERAPY SYSTEM

CROSS-REFERENCE TO RELATED APPLICATIONS

This application is a divisional application of U.S. patent application filed on Aug. 31, 2010 and having application Ser. No. 12/872,973, the entire contents of which are hereby incorporated herein by reference.

BACKGROUND OF THE INVENTION

1. Field of the Invention

The present invention relates to a negative pressure wound therapy system, especially to a therapy system creating negative pressure in the wound environment to promote healing in wounds.

2. Description of the Prior Arts

Negative pressure wound therapy utilizes wound sheets, soft suction pads, or biocompatibility pore materials to attach on the wounds and connects to a vacuum pump. The vacuum pump creates negative pressure in the wound to extract the pus and infection subjects and to draw the healthy tissue fluid so that a moist therapy environment is maintained. Therefore, the blood circulation around the wound is promoted to accelerate wound healing.

One of the conventional negative pressure wound therapy systems has a rigid collector connecting to a front end of the vacuum pump to extract the pus and the infection subjects into the rigid collector. A negative pressure sensor detects the negative pressure in the collector to determine whether the traditional system is operated normally. However, since the vacuum pump is connected to the rear end of the rigid collector, the pump is further from the wound so that the pump needs more power to create negative pressure in the wound and to extract the pus and the infection subjects from the wound.

Another conventional negative pressure wound therapy system solves the above problem. The collector is connected to the rear end of the vacuum pump. The vacuum pump is directly connected to the wound sheet attached on the wound so that the vacuum pump uses less power. However, the collector does not have the same negative pressure environment as the wound. Therefore, the negative pressure sensor is not useful to detect.

To overcome the shortcomings, the present invention provides a negative pressure wound therapy system to mitigate or obviate the aforementioned problems.

SUMMARY OF THE INVENTION

The main objective of the present invention is to provide a negative pressure wound therapy system. The system creates a negative pressure environment in the opening of a wound-dressing unit and a positive pressure environment in the collecting bag. Then a positive pressure detecting procedure is proceeded in the positive pressure environment and a negative pressure detecting procedure is proceeded in the negative pressure environment. The detecting results are sent to determine whether a micro pump is stopped.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
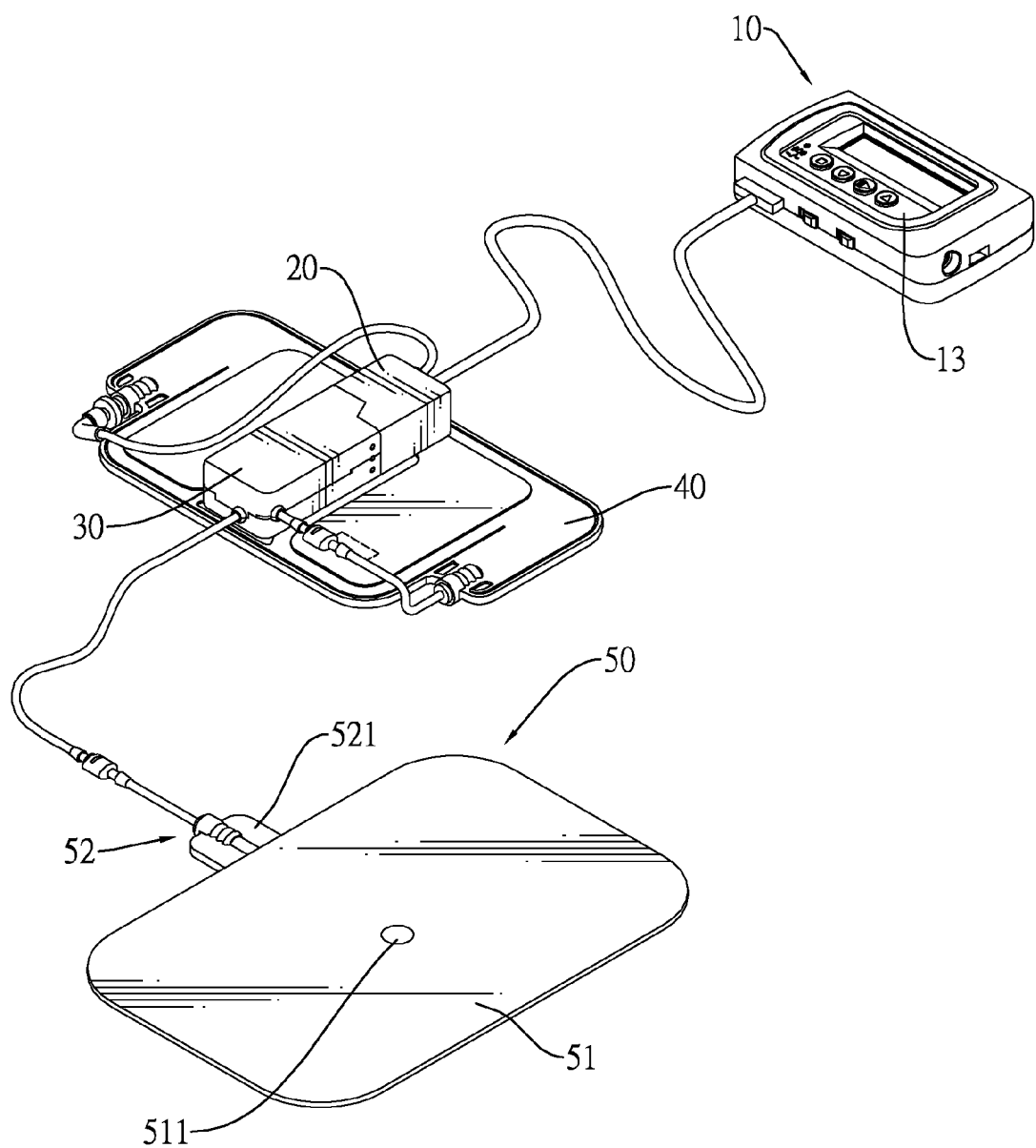
FIG. 1 is a perspective view of a negative pressure wound therapy system in accordance with the present invention.

With reference to FIG. 1, a negative pressure wound therapy system in accordance with the present invention comprises a controller 10, a sensor assembly 20, an actuator 30, a collector 40 and a wound-dressing unit 50.

Figure 2:
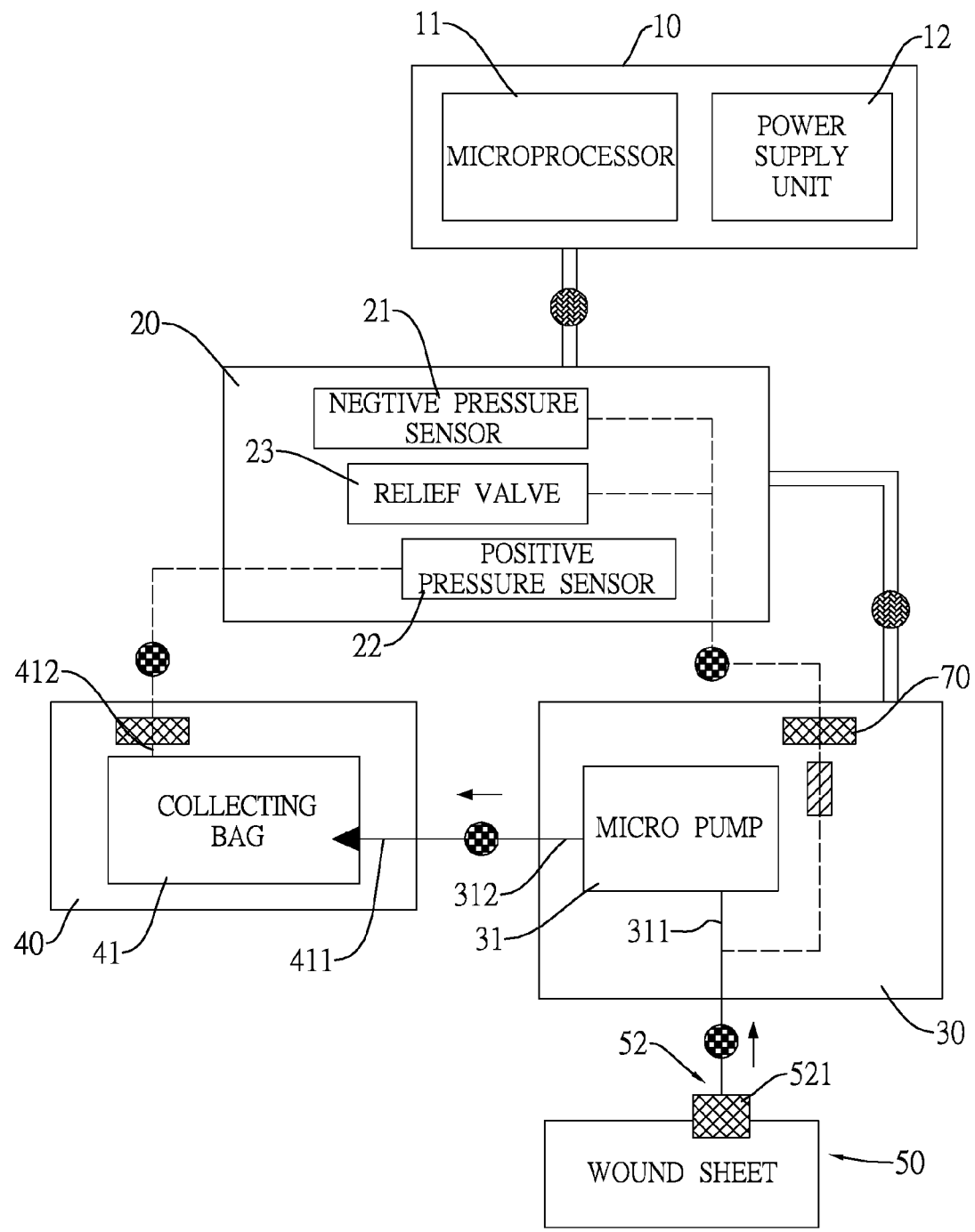
FIG. 2 is a block diagram shown the connection of the negative pressure wound therapy system in FIG. 1.

With reference to FIGS. 1 and 2, the controller 10 comprises a microprocessor 11, a power supply unit 12 and a control panel 13. The power supply unit 12 electrically connects to the microprocessor 11, provides electricity and may be a battery set, or may be a power converter connected to an external power source. The control panel 13 is attached to an outer surface of the controller 10 and electrically connects to the microprocessor 11 and the power supply unit 12.

The sensor assembly 20 comprises a negative pressure sensor 21, a positive pressure sensor 22 and a relief valve 23. The relief valve 23 adjusts the pressure of the system and may apply an intermittent mode.

The actuator 30 comprises a micro pump 31.

The collector 40 comprises a collecting bag 41 and a liquid absorber 42. The liquid absorber 42 is mounted in the collecting bag 41.

Figure 3:
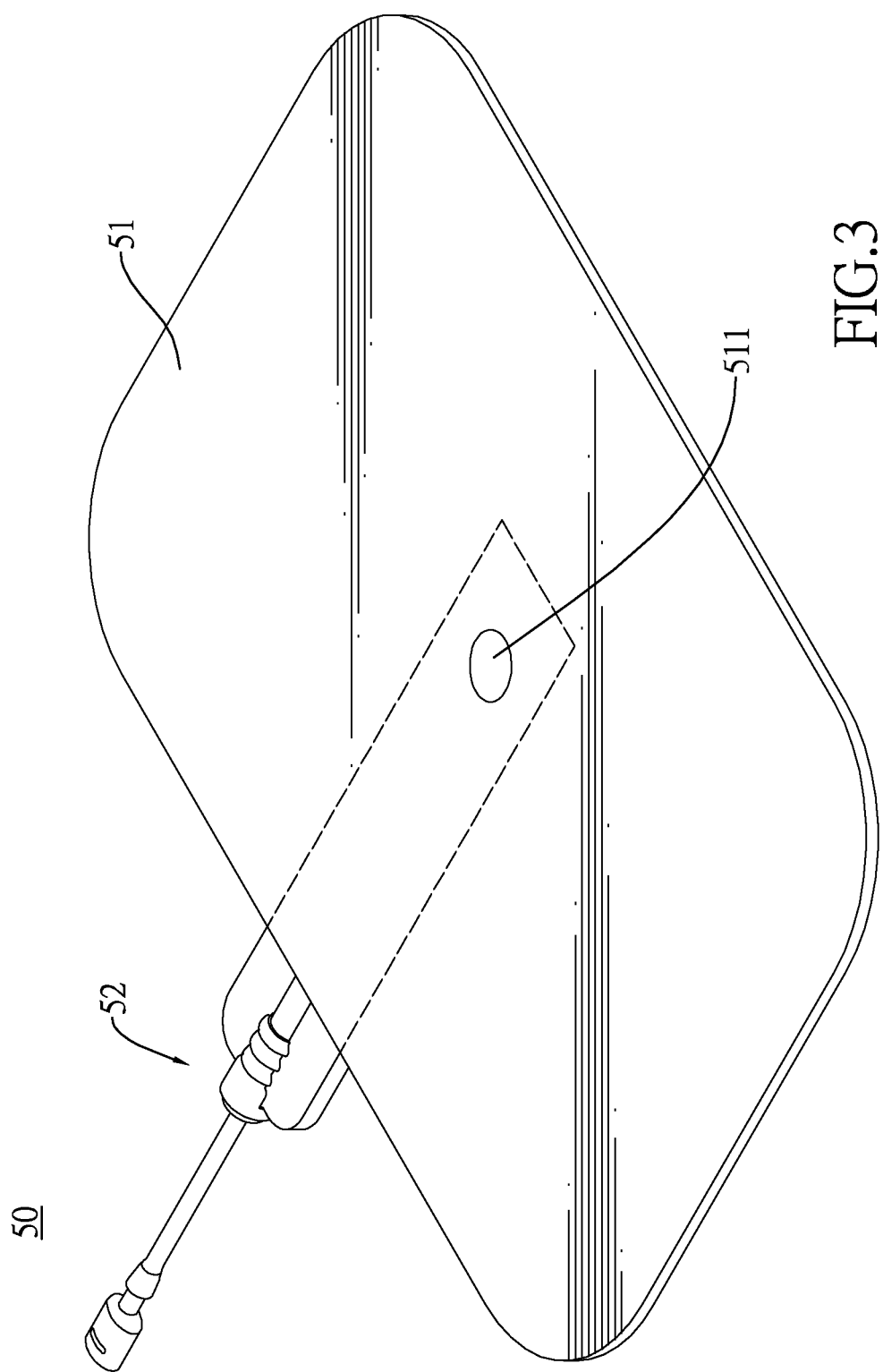
FIG. 3 is a perspective view of a wound-dressing unit of the negative pressure wound therapy system.

With reference to FIG. 3, the wound-dressing unit 50 comprises a wound sheet 51 and a conduit 52. The wound sheet 51 has an opening 511. The conduit 52 is attached securely to the wound sheet 51 and is connected to the opening 511 and has a filter strip 521. The filter strip 521 is made of biocompatibility materials and keeps solid chips such as tissue fragment from flowing into the conduit 52. In a preferred embodiment, the conduit 52 is attached securely to the wound sheet 51 by ultrasonic welding.

Figure 4:
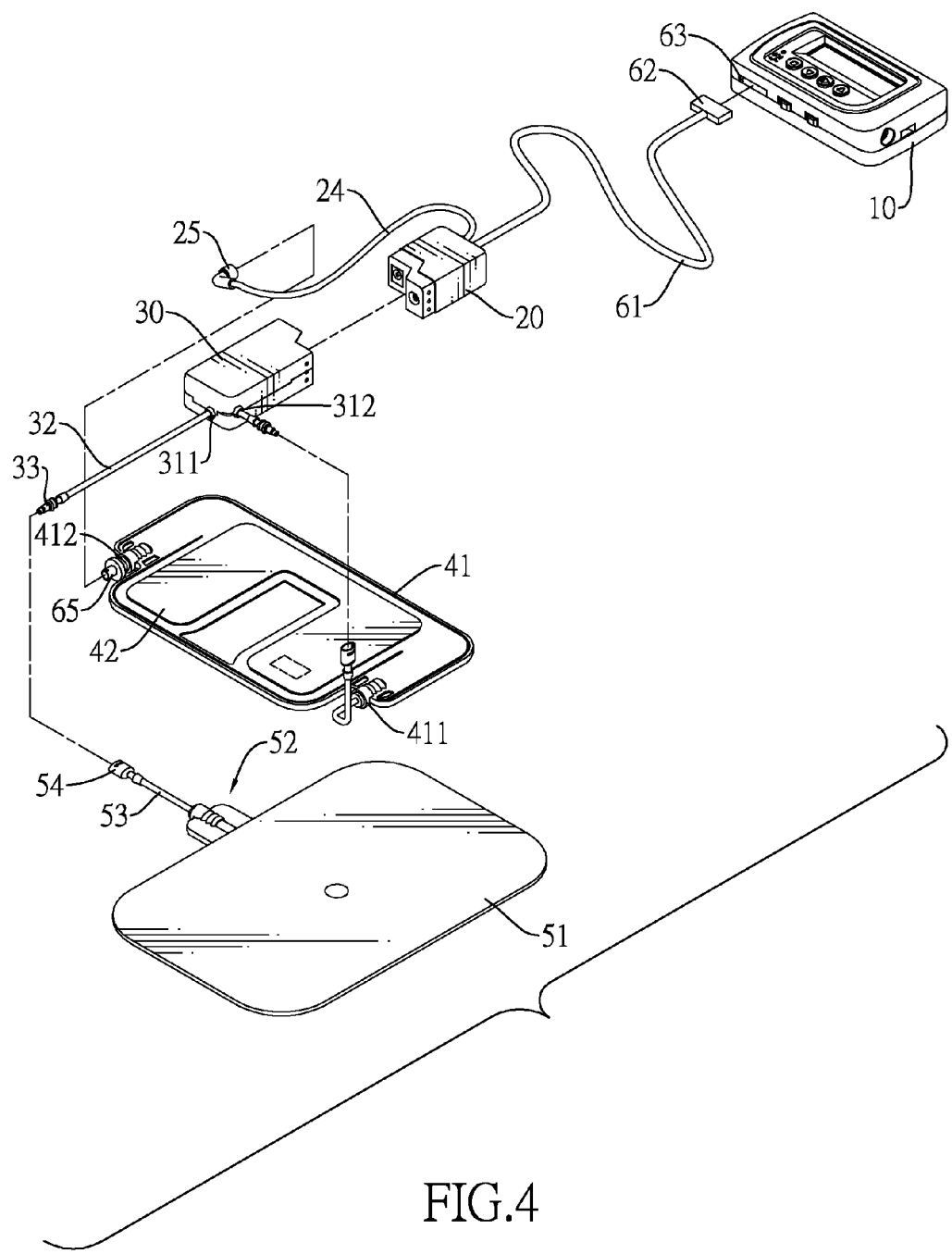
FIG. 4 is an exploded perspective view of the negative pressure wound therapy system in FIG. 1.

With reference to FIGS. 2 and 4, the negative pressure wound therapy system in accordance with the present invention comprises electrical connection and fluid connection to connect aforementioned elements.

The controller 10 is electrically connected to the sensor assembly 20, and the sensor assembly 20 is electrically connected to the actuator 30. Detachable electrical wire set forms the electrical connection. A first detachable electrical wire set connects between the sensor assembly 20 and the controller 10. A second detachable electrical wire set connects between the sensor assembly 20 and the micro pump 31. For example, the first detachable electrical wire set has an electrical wire 61 with a plug 62 protruding out from the sensor assembly 20. The controller 10 has a corresponding socket 63. The plug 62 is plugged detachably into the socket 63 to form the electrical connection.

A fluid connection is formed between the pump inlet 311 of the micro pump 31 and the conduit 52. A fluid connection is formed between the pump outlet 312 of the micro pump 31 and the entry end of the collecting bag 41. A check valve is mounted in the entry end 411 of the collecting bag 41 to keep the liquid in the collecting bag 41 from flowing back to infect the wound. Detachable fluid tube set forms the fluid connections. A first detachable tube set connects between the pump inlet 311 of the micro pump 31 and the sensor assembly 20. A second detachable tube set connects between a detecting end 412 of the collecting bag 41 and the sensor assembly 20. A third detachable tube set connects between an inlet end of the collecting bag and a pump outlet of the micro pump 31. A fourth detachable tube set connects between the wound-dressing unit 50 and the sensor assembly 20. A fifth detachable tube set connects between the wound-dressing unit 50 and the pump inlet 311 of the micro pump 31. For example, a first tube 32 with a fluid connector 33 protrudes out from the micro pump 31 and a second tube 53 with a fluid connector 54 protrudes out from the conduit 52. The fluid connectors 33, 54 detachably connect to each other to form the fluid connection.

A fluid connection is formed between the positive pressure sensor 22 and the detecting end 412 of the collecting bag 41. A fluid connection is formed between the negative pressure sensor 21, the relief valve 23 and the conduit 52, especially through the pump inlet 311 of the micro pump 31. Detachable tube set forms the fluid connections. For example, a tube 24 with a first fluid connector 25 protrudes out from the positive pressure sensor 22. A second fluid connector 65 is mounted on the detecting end 412 of the collecting bag 41. The fluid connectors 25, 65 detachably connect to each other to form the fluid connection.

The controller 10 is electrically connected to the sensor assembly 20, and the sensor assembly 20 is electrically connected to the actuator 30. Detachable electrical wire set forms the electrical connection. A first detachable electrical wire set connects between the sensor assembly 20 and the controller 10. A second detachable electrical wire set connects between the sensor assembly 20 and the micro pump 31. For example, the first detachable electrical wire set has an electrical wire 61 with a plug 62 protruding out from the sensor assembly 20. The controller 10 has a corresponding socket 63. The plug 62 is plugged detachably into the socket 63 to form the electrical connection.

A fluid connection is formed between the pump inlet 311 of the micro pump 31 and the conduit 52. A fluid connection is formed between the pump outlet 312 of the micro pump 31 and the entry end of the collecting bag 41. A check valve is mounted in the entry end 411 of the collecting bag 41 to keep the liquid in the collecting bag 41 from flowing back to infect the wound. Detachable fluid tube set forms the fluid connections. A first detachable tube set connects between the pump inlet 311 of the micro pump 31 and the sensor assembly 20. A second detachable tube set connects between a detecting end 412 of the collecting bag 41 and the sensor assembly 20. A third detachable tube set connects between an inlet end of the collecting bag and a pump outlet of the micro pump 31. A fourth detachable tube set connects between the wound-dressing unit 50 and the sensor assembly 20. A fifth detachable tube set connects between the wound-dressing unit 50 and the pump inlet 311 of the micro pump 31. For example, a first tube 32 with a fluid connector 33 protrudes out from the micro pump 31 and a second tube 64 53 with a fluid connector 54 protrudes out from the conduit 52. The fluid connectors 33, 54 detachably connect to each other to form the fluid connection.

A fluid connection is formed between the positive pressure sensor 22 and the detecting end 412 of the collecting bag 41. A fluid connection is formed between the negative pressure sensor 21, the relief valve 23 and the conduit 52, especially through the pump inlet 311 of the micro pump 31. Detachable tube set forms the fluid connections. For example, a tube 24 with a first fluid connector 25 protrudes out from the positive pressure sensor 22. A second fluid connector 65 is mounted on the detecting end 412 of the collecting bag 41. The fluid connectors 25 65 detachably connect to each other to form the fluid connection.

Figure 5:
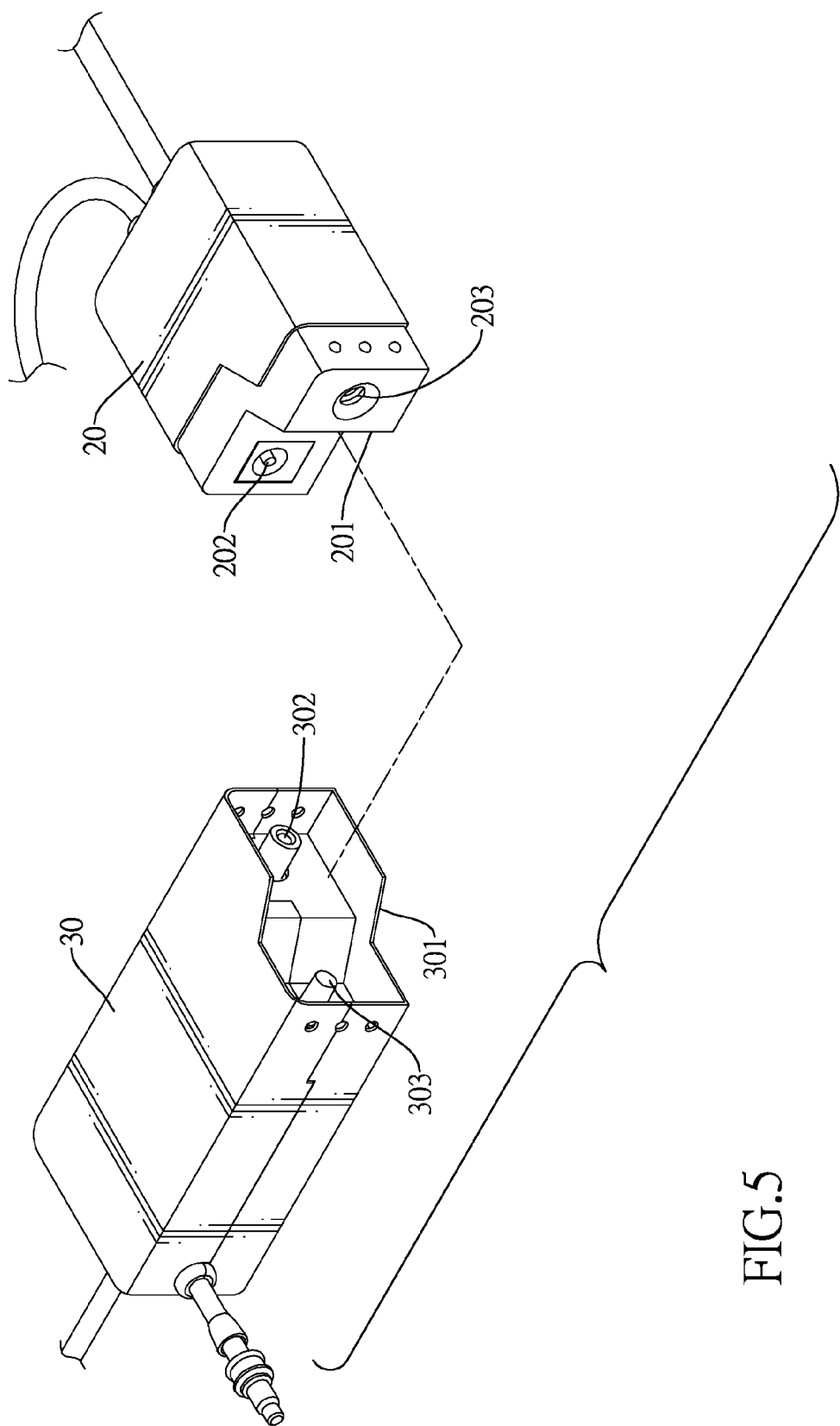
FIG. 5 is an exploded perspective view of a sensor assembly and an actuator of the negative pressure wound therapy system in FIG. 1.
Figure 6:
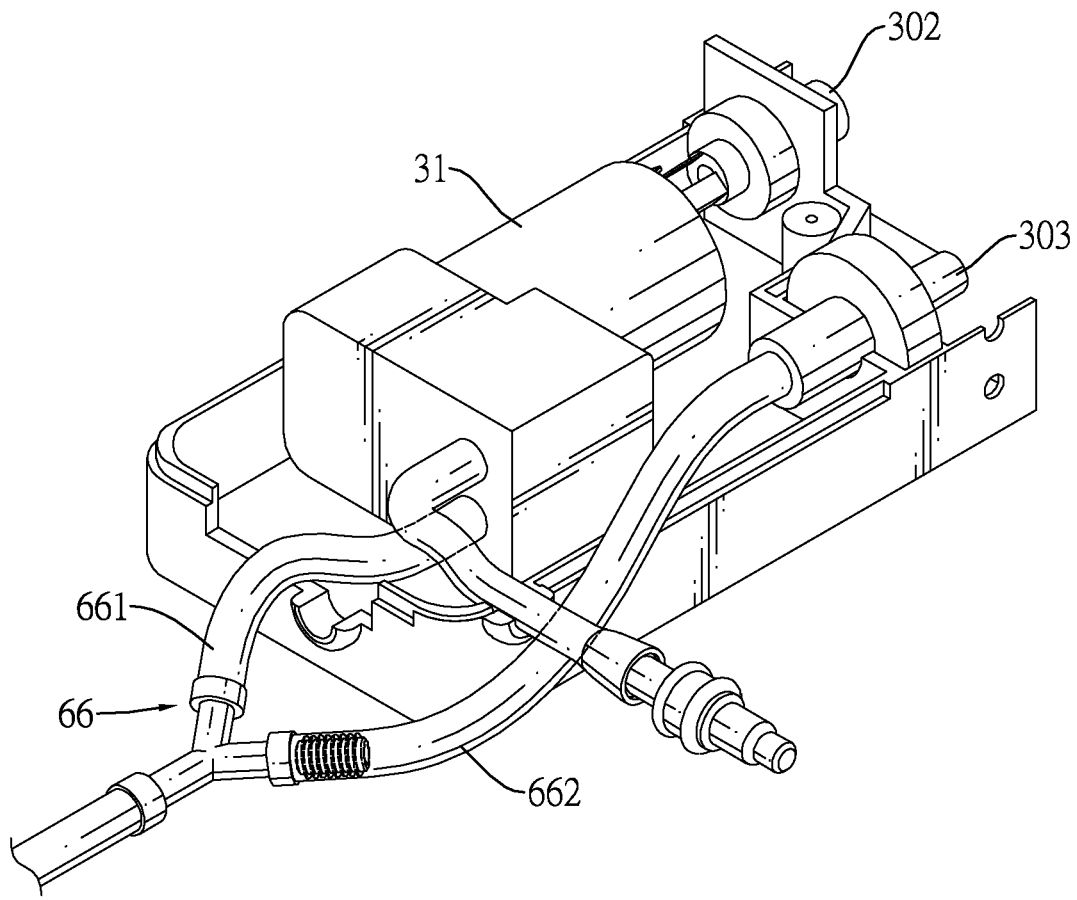
FIG. 6 is a partial perspective view of the actuator of the negative pressure wound therapy system in FIG. 1.

With reference to FIGS. 5 and 6, in a preferred embodiment the sensor assembly 20 has a first connecting interface 201, and the actuator 30 has a second connecting interface 301. The first connecting interface 201 has a first electrical connector 202 and a first fluid connector 203. The second connecting interface 301 has a second electrical connector 302 and a second fluid connector 303. The micro pump 31 is electrically connected to the second electrical connector 302. The connecting interfaces 201, 301 are connected detachably to each other. The first electrical connector 202 is connected to the second electrical connector 302. The first fluid connector 203 is connected to the second fluid connector 303. A fluid division 66 may be a manifold and comprises a first passage 661 and a second passage 662. The first passage 661 connects the pump inlet 311 of the micro pump 31 and the conduit 52. The second passage 662 connects the second fluid connector 303 and the conduit 52.

Furthermore, filters 70 are mounted in the detecting end 412 of the collecting bag 41 and the second fluid connector 303 of the actuator 30 to keep the infections from flowing into the sensor assembly 20.

With the aforementioned electrical connections and the fluid connections being detachably, the elements are available to detach from each other to be repaired independently.

When the system as described is operated, the wound sheet 51 covers the wound of the patient with the opening 511 facing the wound. The user actuates the micro pump 31 through the control panel 13. The micro pump 31 creates a negative pressure environment in the wound through the fluid connections and extracts the pus and infection subjects from the wound. The pus and infection subjects pass through the actuator 30 and are collected in the collecting bag 41.

The system as described has following advantages.

1. Since all of the components connect to each other by detachable electrical wire sets and detachable tube sets, each component is available to be disassembled and repaired independently.

2. The components have different lifespan. For example, the collector 40 and the wound-dressing unit 50 directly contact the infections so that the collector 40 and the wound-dressing unit 50 need to be replaced frequently while the controller 10, the actuator 30 and the sensor assembly 20 can be used for a long time. Therefore, the detachable connections are convenient for users to disassemble and replace each component.

3. When the user moves between different places such as hospital and home, the detachable connections allow the user only bring some of the components to move. For example, the user only carries the controller 10, the sensor assembly 20 and the actuator 30, and leaves the collectors 40 and the wound-dressing units 50 at different places, and vice versa. Therefore, the user only needs to carry part of the system.

4. In the fluid connections, the actuator 30 is located in front of the collecting bag 41. The micro pump 31 is directly connected to the wound sheet attached on the wound so that the micro pump uses less power.

To ensure the system as described is operated safely, a feedback control method in accordance with the present invention for the system as described comprises a test mode and an operating mode.

Figure 7:
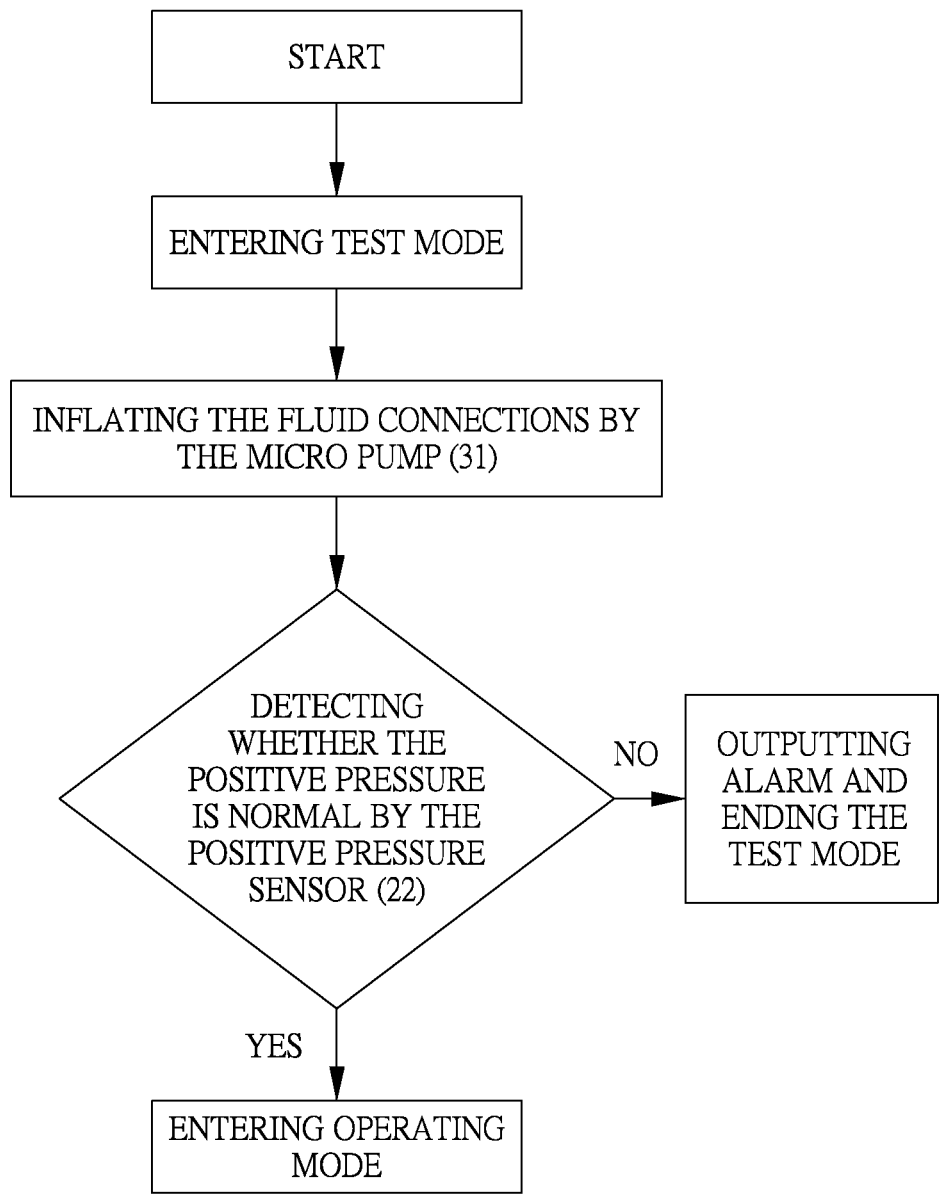
FIG. 7 is a flow chart shown test mode of a feedback control method in accordance with the present invention for the negative pressure wound therapy system in FIG. 1.

With reference to FIG. 7, when the system as described is started, the system enters the test mode. The micro pump 31 inflates the fluid connections in the system. Then the positive pressure sensor 22 detects whether the positive pressure at the detecting end 412 of the collecting bag 41 is normal. When the fluid connections are not connected properly, the positive pressure is abnormal. If the positive pressure is abnormal, the system outputs an alarm signal. Then the test mode is ended. When the fluid connections are connected properly, the positive pressure is normal. If the positive pressure is normal, the system enters the operating mode.

Figure 8:
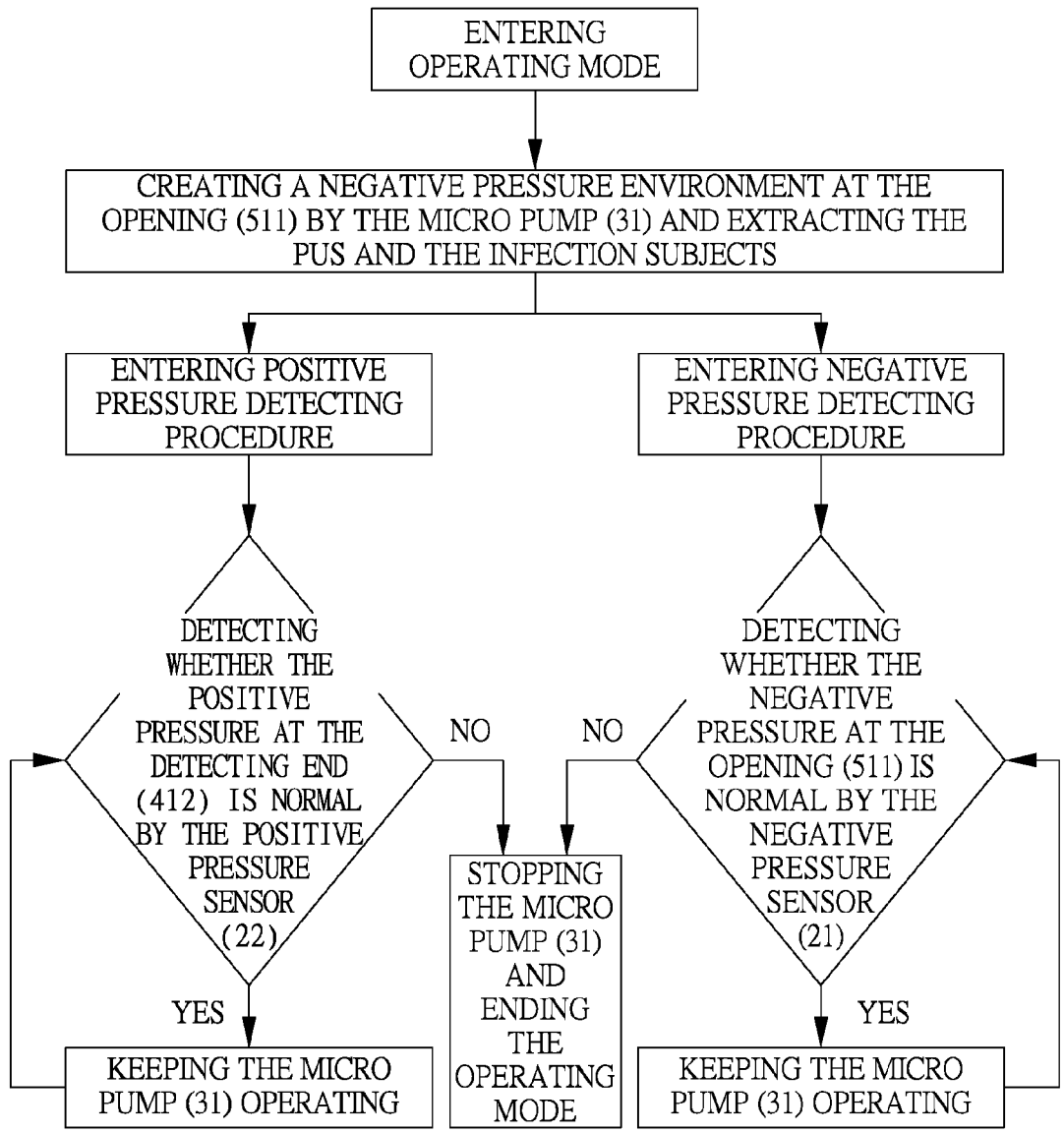
FIG. 8 is a flow chart shown operating mode of the feedback control method for the negative pressure wound therapy system in FIG. 1.

With reference to FIG. 8, when the system enters the operating mode, the micro pump 31 creates a negative pressure environment in the wound through the opening 511 of the wound sheet 51 and extracts the pus and infection subjects from the wound. Then the collecting bag 41 is accordingly formed as a positive pressure environment. Then the positive pressure detecting procedure and negative pressure detecting procedure are started.

The positive pressure detecting procedure detects the positive pressure in the collecting bag 41. The positive pressure sensor 22 detects whether the positive pressure in the collecting bag 41 is normal. When the fluid connections between the collecting bag 41 and other elements are disconnected, or an external overload is applied to the collecting bag 41, or the collecting bag 41 is full of liquid, the positive pressure of the detecting end 412 of the collecting bag 41 is abnormal. If the positive pressure is abnormal, the positive pressure sensor 22 sends a signal to the microprocessor 11 to stop the micro pump 31 and send an alarm signal to notify the user. Therefore, the pus and the infection subjects are prevented from leaking out of the fluid connections or the collecting bag 41 is prevented from breaking because of overload or being full. Then the operating mode is ended. If the positive pressure is normal, the positive pressure sensor 22 keeps processing the positive pressure detecting procedure.

The negative pressure detecting procedure detects the negative pressure in the wound. The negative pressure sensor 21 detects whether the negative pressure in the opening 511 of the wound sheet 51 is normal. When the fluid connections is obstructed or is disconnected, the negative pressure is abnormal. If the negative pressure is abnormal, the negative pressure sensor 21 sends a signal to the microprocessor 11 to stop the micro pump 31 and send an alarm signal to notify the user. If the negative pressure is normal, the negative pressure sensor 23 keeps processing the positive pressure detecting procedure.

With the aforementioned modes, the system as described is operated safely.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A negative pressure wound therapy system comprising:
   a controller;
   a sensor assembly electrically connected to the controller and comprising a negative pressure sensor and a positive pressure sensor to detect pressure, and comprising a relief valve;
   an actuator comprising a micro pump electrically connected to the sensor assembly;
   a collector comprising a collecting bag;
   a wound-dressing unit having an opening;
   a first fluid connection connecting between the sensor assembly and the collecting bag;
   a second fluid connection connecting between the sensor assembly and the wound-dressing unit;
   a third fluid connection connecting between the wound-dressing unit, the actuator and the collecting bag, wherein the actuator is located between the wound-dressing unit and the collecting bag in the third fluid connection;
   whereby the micro pump creates a negative pressure environment in the opening through the third fluid connection and extracts the fluid from the opening of the wound-dressing unit, and the fluid passes the actuator to flow into the collecting bag, and the collecting bag is defined as a positive pressure environment.

2. The negative pressure wound therapy system as claimed in claim 1 further comprising:
   a first detachable electrical wire set connecting between the sensor assembly and the controller;
   a second detachable electrical wire set connecting between the sensor assembly and the micro pump;
   a first detachable tube set connecting between a pump inlet of the micro pump and the sensor assembly;
   a second detachable tube set connecting between a detecting end of the collecting bag and the sensor assembly;
   a third detachable tube set connecting between an inlet end of the collecting bag and a pump outlet of the micro pump;
   a fourth detachable tube set connecting between the wound-dressing unit and the sensor assembly; and
   a fifth detachable tube set connecting between the wound-dressing unit and the pump inlet of the micro pump, wherein
   the first fluid connection is formed by the second detachable tube set;
   the second fluid connection is formed by the fourth detachable tube set; and
   the third fluid connection is formed by the first, third and fifth detachable tube sets.

3. The negative pressure wound therapy system as claimed in claim 2, wherein
   the wound-dressing unit comprises
      a wound sheet, where the opening of the wound-dressing unit is formed through; and
      a conduit attached securely to the wound sheet, connected to the opening and having a filter strip made of biocompatible materials;
   the fourth detachable tube set connects between the conduit and the negative pressure sensor and the relief valve; and
   the fifth detachable tube set connects between the conduit and the pump inlet of the micro pump.

4. The negative pressure wound therapy system as claimed in claim 3 further comprising a fluid division, wherein
   the sensor assembly has a first connecting interface having a first electrical connector and a first fluid connector; and
   the actuator has a second connecting interface connected detachably to the first connecting interface and having a second electrical connector electrically connected to the micro pump connected to the first electrical connector; and a second fluid connector connected to the first fluid connector;

the fluid division comprises a first passage connecting the pump inlet of the micro pump and the conduit; and a second passage connecting the second fluid connector and the conduit.

5. The negative pressure wound therapy system as claimed in claim 3, wherein the fifth detachable tube set comprises a first tube with a fluid connector protruding out from the micro pump and a second tube with a fluid connector protruding out from the conduit, and the fluid connectors detachably connect to each other.

6. The negative pressure wound therapy system as claimed in claim 4, wherein the fifth detachable tube set comprises a first tube with a fluid connector protruding out from the micro pump and a second tube with a fluid connector protruding out from the conduit, and the fluid connectors detachably connect to each other.

7. The negative pressure wound therapy system as claimed in claim 6, wherein the second detachable tube set comprises a tube with a first fluid connector protruding out from the positive pressure sensor and a second fluid connector mounted on the detecting end of the collecting bag, and the fluid connectors detachably connect to each other.

8. The negative pressure wound therapy system as claimed in claim 7 further comprising two filters respectively mounted in the detecting end of the collecting bag and the second fluid connector of the actuator to keep infections from flowing into the sensor assembly.

9. The negative pressure wound therapy system as claimed in claim 8 further comprising a check valve mounted in an entry end of the collecting bag to keep liquid in the collecting bag from flowing back.

* * * * *